United States Patent [19]

Netto

[11] Patent Number: 4,573,999

[45] Date of Patent: Mar. 4, 1986

[54] HUMAN BREAST PROSTHESIS

[76] Inventor: Daniel J. Netto, 153 N. Vendome St., Los Angeles, Calif. 90026

[21] Appl. No.: 541,994

[22] Filed: Oct. 14, 1983

[51] Int. Cl.$^4$ ................................................ A61F 1/00
[52] U.S. Cl. ............................................. 623/7; 623/11
[58] Field of Search ......................... 3/36, 1; 128/92 C

[56] References Cited

U.S. PATENT DOCUMENTS 2,543,499  2/1951  Kaush ........................................ 3/36

FOREIGN PATENT DOCUMENTS 2457041  6/1976  Fed. Rep. of Germany ............ 3/36
792692   4/1958  United Kingdom ....................... 3/36

OTHER PUBLICATIONS

McGhan, "Mammary Implant", Santa Barbra, Calif., 1979/Sep.

Primary Examiner—Richard J. Apley
Assistant Examiner—David Isabella
Attorney, Agent, or Firm—Fulwider, Patton, Rieber, Lee & Utecht

[57] ABSTRACT

A prosthetic implant for human breasts, comprising a fluid or gel filled body, the surface of which has waves arranged in a concentric pattern rather than a smooth configuration. The amplitude of the waves reduces under the pressure of capsular contracture, thereby relieving said pressure without reducing the volume or firmness of the implant.

7 Claims, 7 Drawing Figures

HUMAN BREAST PROSTHESIS

CROSS-REFERENCE TO RELATED APPLICATIONS

I have not filed any other patent applications related to the invention disclosed in this Application.

BACKGROUND

1. Field of the Invention

This invention is in the general field of prosthetic devices, and more particularly in the field of surgical prosthetic implants for human breasts or the like.

A prosthetic human breast implant is a device made of silicone or the like and surgically placed within the breast so as to increase the size of firmness thereof. It is known to persons skilled in the art, especially plastic surgeons, that a growth of myofibroblast fibers occurs after surgery and, for a period of several weeks thereafter, the fibers usually grow until they completely surround the prosthetic implant. The fibrous growth frequently becomes so dense that considerable pressure is exerted on the implant, causing discomfort or in some cases acute pain to the patient.

Surgeons occasionally implant prosthetic devices in other parts of the body for cosmetic or reconstructive purposes, and a similar growth of fiber and resulting pressure and pain occurs when such a procedure is carried out.

If the prosthetic implant were designed to contract under pressure, then the pain would be alleviated. However, this solution to the problem is not feasible because the whole idea of implanting the prosthesis is to achieve a pre-determined increase in size or firmness in the breast or other part of the body, and a prosthesis that would shrink under pressure would fail to perform its intended function.

2. Prior Art

Some prosthetic devices are hollow, consisting of a silicone outer shell filled with fluid. It is known to persons skilled in the art that the pain caused by the pressure exerted by the fibrous growth can be treated by injection of a growth-inhibiting drug into the fluid, which drug diffuses through the fluid and the outer shell and then inhibits the growth of the fibers. However, this treatment is only temporary and in many cases does not give adequate relief.

SUMMARY OF THE INVENTION

I have carefully studied the problem of how to give permanent relief from the discomfort and pain caused by the pressure of the growth of fibers against the prosthetic implant. I have conceived and developed a new invention which accomplishes this objective.

My invention can be described as a prosthetic implant, the surface of which, rather than being smooth, comprises a series of concentric waves. The growth of the fibers across and around the implant exerts pressure on the peaks of the waves but not on the troughs. As the pressure increases, the surface of the prosthesis deforms under pressure; the peaks of the waves compress under pressure from the contracture of the fiber growth, while the troughs, which are not under pressure from the contracture of the fiber growth, become shallower. In this fashion, the pressure on the prosthetic device is relieved by the action of the prosthetic device in changing its shape. The patient is not uncomfortable, and yet the prosthetic device does not shrink or change in firmness.

It is an object of this invention to provide a human breast or other prosthetic implant which will change its shape under pressure so as to alleviate the discomfort caused by the pressure of the growth of myofibroblast fibers during the weeks after surgery.

It is a further object of this invention to provide such a prosthesis which will maintain the desired size and firmness during the period of fibrous growth and after the fibrous growth has ceased.

The foregoing, and other objects and advantages of this invention, will become apparent to those skilled in the art upon reading the description of the preferred embodiment and reviewing the drawings.

DESCRIPTION OF THE PREFERRED EMBODIMENT

Figure 1:
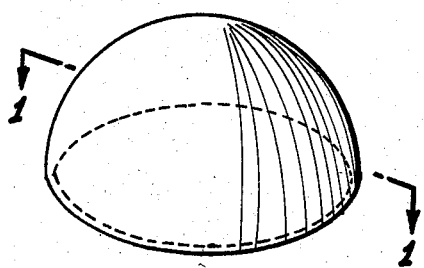
FIG. 1 is a perspective view of a conventional or prior art human breast prosthetic implant.
Figure 2:
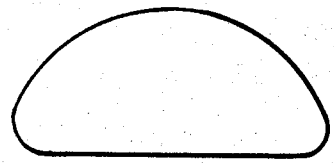
FIG. 2 is a cross-section view of the device shown in FIG. 1.

FIG. 1 is a perspective view of a conventional or prior art human breast prosthetic implant, showing the smooth and flat surface. A cross-section of the implant of FIG. 1, along the line 1—1, is shown in FIG. 2. As pressure is exerted by fibrous growth across and around this device, the pressure builds up and causes pain, as there is no way to relieve the pressure short of contraction of the implant.

Figure 3:
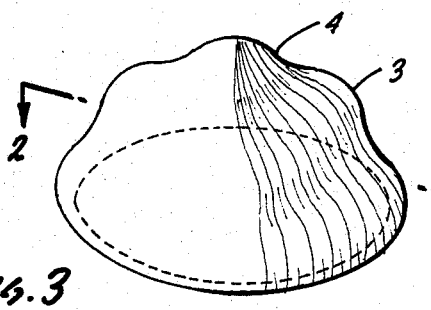
FIG. 3 is a perspective view of my invention, a prosthetic implant with a surface comprising a series of waves.
Figure 4:
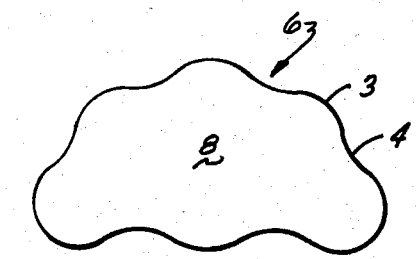
FIG. 4 is a cross-section view of the device shown in FIG. 3.
Figure 5:
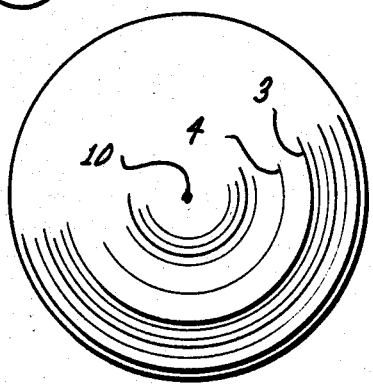
FIG. 5 is a top view of the device shown in FIG. 3.

FIG. 3 is a perspective view of a human breast prosthetic implant embodying my invention. FIG. 4 is a cross-section view along the line 2—2 of FIG. 3, and FIG. 5 is a top view. In my invention, as the fibers grow around and across the implant, pressure is exerted on peaks 3 of the waves, but not on the intervening valleys or troughs 4. As the pressure increases with time, peaks 3 contract and troughs 4 expand, and as this process takes place the amplitude of the waves gets smaller and the surface becomes less wavy. The pressure eventually stops increasing, and the shape of the prosthetic implant then stops changing. At that time, the surface will be nearly smooth, and the remaining waves will be too small in amplitude to be noticeable.

Figure 6:
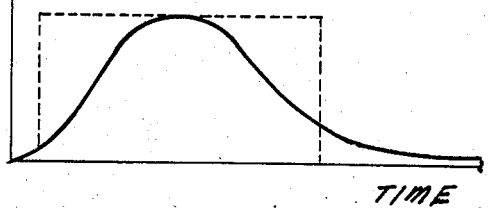
FIG. 6 is a graph, illustrating the tension, or pressure, occurring during the weeks following surgery, exerted on a conventional implant as illustrated in FIG. 1.
Figure 7:
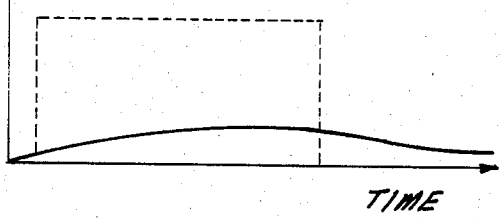
FIG. 7 is a graph, illustrating the tension, or pressure, occurring during the weeks following surgery, exerted on my invention, a prosthetic implant with a surface comprising a series of waves.

In FIG. 6, the pressure caused by the growth of fibers around a conventional implant is shown. During the weeks following the surgical implant, there is a large increase in pressure, causing pain and discomfort. By contrast, FIG. 7 shows how my invention reduces the pressure to such an extent that in most cases there will be no discomfort at all.

In the preferred embodiment, my invention is made of a generally hemispheric outer covering 6 of silicone or the like, which embodies the waves or undulations that define the peaks 3 and troughs 4. The interior is filled with a filling material such as a viscous fluid or a gelatin-like material 8. As seen in FIG. 3 through FIG. 5, the undulations in the exteriorly directed surface of the covering 6 are circumferentially continuous and arranged in a concentric pattern about the polar axis 10.

The construction of my invention is sufficiently rigid that the implant will maintain its firmness except under the considerable pressure exerted by the fibrous growth, and under this pressure the peaks of the waves in the surface of the prosthesis slowly decrease in amplitude, and the troughs slowly expand outward.

In an alternative embodiment, the implant is a unitary body with fluid, being constructed of a substance 8 which deforms only under sustained pressure.

The exact amplitude and length of the waves are not critical and will vary, depending on the size and firmness of the implant as selected by the surgeon. However, on a human breast implant of average size (about four inches across and two inches high) the wavelength will be about one-half to three-quarters of an inch, and the amplitude will be about one-fourth to one-half inch.

While the embodiment shown and described is fully capable of achieving the objects and advantages of this invention, it will be apparent that such embodiment is not exhaustive and is shown for purposes of illustration, not limitation.

I claim:

1. A prosthetic implant for surgical implantation within living tissue, said implant comprising body means having undulations over a substantial portion of its exteriorly directed surface, said undulations defining a plurality of predetermined substantially concentric peaks and intervening valleys about a substantially vertical projection axis, said surface of said body means being made of material sufficiently rigid to maintain the shape of said peaks and valleys in the absence of pressure against said exteriorly directed surface, but yieldable to pressures on said exteriorly directed surface by any fibrous growth which may bridge said valleys, whereby said pressures tend to displace the material of said body means and flatten said peaks rather than acting against any adjacent living tissue.

2. An implant according to claim 1, wherein said body means comprises a filling material and a covering enveloping and containing said filling material.

3. An implant according to claim 2, wherein said filling material is a fluid.

4. An implant according to claim 2, wherein said filling material is a deformable gel.

5. An implant according to claim 1, wherein said exteriorly directed surface is generally hemispherical.

6. An implant according to claim 1, wherein said body means is unitary.

7. A prosthetic implant for surgical implantation underneath the skin of a human chest to create the apperance of a female breast, said implant comprising:

a filling material; and a covering enveloping and containing said filling material, said covering having undulations over a substantial portion of its exteriorly directed surface, said undulations defining a plurality of predetermined substantially concentric peaks and intervening valleys about a substantially vertical projection axis, said covering being made of material sufficiently rigid to maintain the shape of said peaks and valleys in the absence of pressure against said exteriorly directed surface, but yieldable to pressures on said exteriorly directed surface by any fibrous growth which may bridge said valleys, whereby said pressures tend to displace said filling material and flatten said peaks rather than acting against any adjacent chest tissue.

* * * * *